(12) United States Patent
Lin et al.

(10) Patent No.: US 8,129,181 B2
(45) Date of Patent: Mar. 6, 2012

(54) F1B-TMIR PLASMID VECTOR AND TRANSGENIC MOUSE

(75) Inventors: Kurt M. Lin, Taipei (TW); Ing-Ming Chiu, Miaoli (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 12/460,797

(22) Filed: Jul. 24, 2009

(65) Prior Publication Data

US 2011/0023136 A1 Jan. 27, 2011

(51) Int. Cl.
  *C12N 15/00* (2006.01)
  *C07H 21/04* (2006.01)
  *A01K 67/00* (2006.01)

(52) U.S. Cl. ............... 435/320.1; 536/23.4; 536/24.1

(58) Field of Classification Search .................. None
  See application file for complete search history.

(56) References Cited

U.S. PATENT DOCUMENTS

| 6,984,518 | B2 | 1/2006 | Chiu | |
|---|---|---|---|---|
| 7,045,678 | B2 | 5/2006 | Chiu | |
| 2006/0277613 | A1* | 12/2006 | Gambhir et al. | 800/8 |
| 2007/0061908 | A1 | 3/2007 | Chiu | |
| 2009/0176260 | A1* | 7/2009 | Wu et al. | 435/8 |

OTHER PUBLICATIONS

Kesarwala, A.H, et al. Piwnica-Worms D. Second-generation triple reporter for bioluminescence, micro-positron emission tomography, and fluorescence imaging. Mol Imaging. Oct.-Dec. 2006;5(4):465-474.

Kim, Y.J, et al. Multimodality imaging of lymphocytic migration using lentiviral-based transduction of a tri-fusion reporter gene. Mol Imaging Biol. Sep.-Oct. 2004;6(5):331-340.

Ponomarev, V., et al. A novel triple-modality reporter gene for whole-body fluorescent, bioluminescent, and nuclear noninvasive imaging. Eur J Nucl Med Mol Imaging. May 2004;31(5):740-751.

Ray, P., et al. Imaging tri-fusion multimodality reporter gene expression in living subjects. Cancer Res. Feb. 15, 2004;64(4):1323-1330.

Myers, R.L., et al. Functional characterization of the brain-specific FGF-1 promoter, FGF-1.B. J Biol Chem. Apr. 7, 1995;270(14):8257-8266.

Chotani, M.A., et al. Human fibroblast growth factor 1 gene expression in vascular smooth muscle cells is modulated via an alternate promoter in response to serum and phorbol ester. Nucleic Acids Res. Feb. 11, 1995;23(3):434-441.

Alam, K.Y., Characterization of the 1B promoter of fibroblast growth factor 1 and its expression in the adult and developing mouse brain. J Biol Chem. Nov. 22, 1996;271(47):30263-30271.

Chiu, I.M., et al. Tumorigenesis in transgenic mice in which the SV40 T antigen is driven by the brain-specific FGF1 promoter. Oncogene. Dec. 14, 2000;19(54):6229-6239.

Lin, K.M., et al. Human breast tumor cells express multimodal imaging reporter genes. Mol Imaging Biol. Sep. 2008;10(5):253-263.

Tong, R., et al. The universal donor mouse: a mouse expressing a tri-fusion reporter gene in all tissues. World Molecular Imaging Conference. Nice, France; 2008:0911.

* cited by examiner

*Primary Examiner* — Quang Nguyen

(74) *Attorney, Agent, or Firm* — Baker & McKenzie LLP

(57) ABSTRACT

A trifusion reporter plasmid is described that comprises a plasmid operably coupled to a mammalian FGF1B promoter that is operably coupled to a bioluminescence gene fused to a fluorescence gene fused to a nuclear medical imaging gene. The new reporter allows in vivo or ex vivo detection of gene expression in three different ways, in addition to traditional in vitro detection methods. Transgenic animals containing this new trifusion reporter and uses of same are described.

1 Claim, 10 Drawing Sheets
(7 of 10 Drawing Sheet(s) Filed in Color)

FIG 7A: SEQ ID NO 1

```
GGGAGGTCCC TTTCATCCAG CAGCCTTCTG ACTCCAGAGG AGAGTCTCCG AGCCACGACC      60
TGCTGTTTCC CTGGCAACTC AGGCCTCAAA ATAAACAGGA TTCTGCTCAG ACGGGCCAGA     120
AGTCCATTCG GCTCACACAT TTGCCCCAAG ACAAACCACG TTAAAATAAC ACCCAGGGTA     180
GCTGCTGCCA CCGTCTTCTG TCTCTACCTC CCTCCTGGCT GGCCAATGGC TCTGTGTTCC     240
TGGGCCTGCT GCTGGCTGTC CAGAGTAGGG GTTGCTTAGA GCTGTGTGCA TCCCTGCGGG     300
TGGTGTGGGA GTGGGCGGTT GTCTAAAGGC AGGTCCCCTC TACTGATAAA CAAGGACCGG     360
AGATAGACCT AGAGGCTGAC ATTCTTGGCT CCCCCAGCCT ACACCCCCCC CACCTCGATT     420
TCCCACAGAG CCCTAGGGAC GGGTAGCCAG CTCTGTGGCA TGGTATCTGG AGGCAGGCCA     480
GCAACCTGAT GTGCATGCCA CGGCCCGTCC CTCTCCCAC TCAGAGCTGC AGTAGCCTGG      540
AGGTTCAGAG AGCCGGGCTA CTCTGAGAAG AAGACACGAT CTAAGTAAGC TTCGAATTCT     600
GCAGTCGACG GTACCGCGGG CCCGGGATCC ACCGGTCACC ATGGAAGACG CCAAAAACAT     660
AAAGAAAGGC CCGGCGCCAT TCTATCCTCT AGAGGATGGA ACCGCTGGAG AGCAACTGCA     720
TAAGGCTATG AAGAGATACG CCCTGGTTCC TGGAACAATT GCTTTTACAG ATGCACATAT     780
CGAGGTGAAC ATCACGTACG CGGAATACTT CGAAATGTCC GTTCGGTTGG CAGAAGCTAT     840
GAAACGATAT GGGCTGAATA CAAATCACGA AATCGTCGTA TGCAGTGAAA ACTCTCTTCA     900
ATTCTTTATG CCGGTGTTGG GCGCGTTATT TATCGGAGTT GCAGTTGCGC CCGCGAACGA     960
CATTTATAAT GAACGTGAAT TGCTCAACAG TATGAACATT TCGCAGCCTA CCGTAGTGTT    1020
TGTTTCCAAA AAGGGGTTGC AAAAAATTTT GAACGTGCAA AAAAAATTAC CAATAATCCA    1080
GAAAATTATT ATCATGGATT CTAAAACGGA TTACCAGGGA TTTCAGTCGA TGTACACGTT    1140
CGTCACATCT CATCTACCTC CCGGTTTTAA TGAATACGAT TTTGTACCAG AGTCCTTTGA    1200
TCGTGACAAA ACAATTGCAC TGATAATGAA TTCCTCTGGA TCTACTGGGT TACCTAAGGG    1260
TGTGGCCCTT CCGCATAGAA CTGCCTGCGT CAGATTCTCG CATGCCAGAG ATCCTATTTT    1320
TGGCAATCAA ATCATTCCGG ATACTGCGAT TTTAAGTGTT GTTCCATTCC ATCACGGTTT    1380
TGGAATGTTT ACTACACTCG GATATTTGAT ATGTGGATTT CGAGTCGTCT TAATGTATAG    1440
ATTTGAAGAA GAGCTGTTTT TACGATCCCT TCAGGATTAC AAAATTCAAA GTGCGTTGCT    1500
AGTACCAACC CTATTTTCAT TCTTCGCCAA AAGCACTCTG ATTGACAAAT ACGATTTATC    1560
TAATTTACAC GAAATTGCTT CTGGGGGCGC ACCTCTTTCG AAAGAAGTCG GGGAAGCGGT    1620
TGCAAAACGC TTCCATCTTC CAGGGATACG ACAAGGATAT GGGCTCACTG AGACTACATC    1680
AGCTATTCTG ATTACACCCG AGGGGGATGA TAAACCGGGC GCGGTCGGTA AAGTTGTTCC    1740
ATTTTTTGAA GCGAAGGTTG TGGATCTGGA TACCGGGAAA ACGCTGGGCG TTAATCAGAG    1800
AGGCGAATTA TGTGTCAGAG GACCTATGAT TATGTCCGGT TATGTAAACA ATCCGGAAGC    1860
GACCAACGCC TTGATTGACA AGGATGGATG GCTACATTCT GGAGACATAG CTTACTGGGA    1920
CGAAGACGAA CACTTCTTCA TAGTTGACCG CTTGAAGTCT TTAATTAAAT ACAAAGGATA    1980
TCAGGTGGCC CCCGCTGAAT GGAATCGAT ATTGTTACAA CACCCCAACA TCTTCGACGC      2040
GGGCGTGGCA GGTCTTCCCG ACGATGACGC CGGTGAACTT CCCGCCGCCG TTGTTGTTTT    2100
GGAGCACGGA AAGACGATGA CGGAAAAAGA GATCGTGGAT TACGTCGCCA GTCAAGTAAC    2160
AACCGCGAAA AAGTTGCGCG GAGGAGTTGT GTTTGTGGAC GAAGTACCGA AAGGTCTTAC    2220
CGGAAAACTC GACGCAAGAA AAATCAGAGA GATCCTCATA AAGGCCAAGA AGGGCGGAAA    2280
GTCCAAATTG AAACCGGTCG CCACCATGGT GAGCAAGGGC GAGGAGCTGT TCACCGGGGT    2340
GGTGCCCATC CTGGTCGAGC TGGACGGCGA CGTAAACGGC CACAAGTTCA GCGTGTCCGG    2400
CGAGGGCGAG GGCGATGCCA CCTACGGCAA GCTGACCCTG AAGTTCATCT GCACCACCGG    2460
CAAGCTGCCC GTGCCCTGGC CCACCCTCGT GACCACCCTG ACCTACGGCG TGCAGTGCTT    2520
CAGCCGCTAC CCCGACCACA TGAAGCAGCA CGACTTCTTC AAGTCCGCCA TGCCCGAAGG    2580
CTACGTCCAG GAGCGCACCA TCTTCTTCAA GGACGACGGC AACTACAAGA CCCGCGCCGA    2640
GGTGAAGTTC GAGGGCGACA CCCTGGTGAA CCGCATCGAG CTGAAGGGCA TCGACTTCAA    2700
GGAGGACGGC AACATCCTGG GGCACAAGCT GGAGTACAAC TACAACAGCC ACAACGTCTA    2760
TATCATGGCC GACAAGCAGA AGAACGGCAT CAAGGTGAAC TTCAAGATCC GCCACAACAT    2820
CGAGGACGGC AGCGTGCAGC TCGCCGACCA CTACCAGCAG AACACCCCCA TCGGCGACGG    2880
CCCCGTGCTG CTGCCCGACA ACCACTACCT GAGCACCCAG TCCGCCCTGA GCAAAGACCC    2940
CAACGAGAAG CGCGATCACA TGGTCCTGCT GGAGTTCGTG ACCGCCGCCG GGATCACTCT    3000
```

FIG 7B: SEQ ID NO 1 CONT

```
CGGCATGGAC GAGCTGTACA AGTCCGGCCG GACTCAGATC TCGAGCTCAA GCTTCGAATT    3060
 CATGCCCACG CTACTGCGGG TTTATATAGA CGGTCCCCAC GGGATGGGGA AAACCACCAC    3120
CACGCAACTG CTGGTGGCCC TGGGTTCGCG CGACGATATC GTCTACGTAC CCGAGCCGAT    3180
GACTTACTGG CGGGTGCTGG GGGCTTCCGA GACAATCGCG AACATCTACA CCACACAACA    3240
CCGCCTCGAC CAGGGTGAGA TATCGGCCGG GGACGCGGCG GTGGTAATGA CAAGCGCCCA    3300
GATAACAATG GGCATGCCTT ATGCCGTGAC CGACGCCGTT CTGGCTCCTC ATATCGGGGG    3360
GGAGGCTGGG AGCTCACATG CCCCGCCCCC GGCCCTCACC CTCATCTTCG ACCGCCATCC    3420
CATCGCCGCC CTCCTGTGCT ACCCGGCCGC GCGGTACCTT ATGGGCAGCA TGACCCCCCA    3480
GGCCGTGCTG GCGTTCGTGG CCCTCATCCC GCCGACCTTG CCCGGCACCA ACATCGTGCT    3540
TGGGGCCCTT CCGGAGGACA GACACATCGA CCGCCTGGCC AAACGCCAGC GCCCCGGCGA    3600
GCGGCTGGAC CTGGCTATGC TGGCTGCGAT TCGCCGCGTT TACGGGCTAC TTGCCAATAC    3660
GGTGCGGTAT CTGCAGTGCG GCGGGTCGTG GCGGGAGGAC TGGGGACAGC TTTCGGGGAC    3720
GGCCGTGCCG CCCCAGGGTG CCGAGCCCCA GAGCAACGCG GGCCCACGAC CCCATATCGG    3780
GGACACGTTA TTTACCCTGT TTCGGGCCCC CGAGTTGCTG GCCCCAACG GCGACCTGTA     3840
TAACGTGTTT GCCTGGGCCT TGGACGTCTT GGCCAAACGC CTCCGTTCCA TGCACGTCTT    3900
TATCCTGGAT TACGACCAAT CGCCCGCCGG CTGCCGGGAC GCCCTGCTGC AACTTACCTC    3960
CGGGATGGTC CAGACCCACG TCACCACCCC CGGCTCCATA CCGACGATAT GCGACCTGGC    4020
GCGCACGTTT GCCCGGGAGA TGGGGGAGGC TAACGGATCC ACCGGATCTA GATAA         4075
```

F1B-TMIR PLASMID VECTOR AND TRANSGENIC MOUSE

CROSS-REFERENCE TO RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a trimodality fusion reporter vector that contains reporter genes for fluorescence, bioluminescence, and nuclear medical imaging, driven by fibroblast growth factor 1B (FGF1B) promoter. Further, the present invention relates to a transgenic mouse expressing such reporters.

BACKGROUND OF THE INVENTION

The greatest advantage of a multimodal imaging is that it combines the strengths of multiple imaging platforms on the same subject. This provides with flexible tools for longitudinal tracing and measurement of delivered transgenes. To take the advantages of multimodal imaging systems, multiple reporter genes have to be expressed in cis or as a single fusion gene product. Multimodality reporters consisting of combinations of fluorescent proteins of various colors (CFP, GFP, YFP, or RFP), bioluminescence (Firefly luciferase or Rennila luciferase), and nuclear medical imaging (Truncated human herpes simplex virus type 1 thymidine kinase (HSV1tk) or sodium iodine symporters) have been previously generated and utilized in numerous applications (see Rome C, Couillaud F, Moonen C T. Gene expression and gene therapy imaging. *Eur Radiol*. February 2007; 17(2):305-319; Kang J H, Chung J K. Molecular-genetic imaging based on reporter gene expression. *J Nucl Med*. June 2008; 49 Suppl 2:164S-179S.)

Functional bi- or tri-modal reporter genes produced by fusing coding regions of fluorescent proteins, luciferase, or HSV1tk were generated and these multimodal reporters driven by a ubiquitous promoter were primarily for oncological applications (see Kesarwala A H, Prior J L, Sun J, Harpstrite S E, Sharma V, Piwnica-Worms D. Second-generation triple reporter for bioluminescence, micro-positron emission tomography, and fluorescence imaging. *Mol. Imaging*. October-December 2006; 5(4):465-474; Kim Y J, Dubey P, Ray P, Gambhir S S, Witte O N. Multimodality imaging of lymphocytic migration using lentiviral-based transduction of a tri-fusion reporter gene. *Mol Imaging Biol*. September-October 2004; 6(5):331-340; Ponomarev V, Doubrovin M, Serganova I, et al. A novel triple-modality reporter gene for whole-body fluorescent, bioluminescent, and nuclear noninvasive imaging. *Eur Nucl Med Mol Imaging*. May 2004; 31(5):740-751; Ray P, De A, Min J J, Tsien R Y, Gambhir S S. Imaging tri-fusion multimodality reporter gene expression in living subjects. *Cancer Res*. Feb. 15, 2004; 64(4):1323-1330).

Fibroblast growth factor 1 (FGF1) also known as acidic fibroblast growth factor (see Wang W P, Lehtoma K, Varban M L, Krishnan I, Chiu I M. Cloning of the gene coding for human class 1 heparin-binding growth factor and its expression in fetal tissues. *Mol Cell Biol*. June 1989; 9(6):2387-2395), is widely expressed in a variety of tissues in different stages of development. While no abnormality was observed in FGF1 null mice indicates highly functional redundancy in FGF family genes that consisting of at least 22 members (see Miller D L, Ortega S, Bashayan O, Basch R, Basilico C. Compensation by fibroblast growth factor 1 (FGF1) does not account for the mild phenotypic defects observed in FGF2 null mice. *Mol Cell Biol*. March 2000; 20(6):2260-2268). FGF1 is the universal FGF and can activate all FGFRs and results in the activation of signal transduction cascades, leading to broad biological processes, including embryonic development, cell growth, morphogenesis and remodeling (see Ornitz D M, Xu J, Colvin J S, et al. Receptor specificity of the fibroblast growth factor family. *J Biol Chem*. Jun. 21, 1996; 271(25):15292-15297; Zhang X, Ibrahimi O A, Olsen S K, Umemori H, Mohammadi M, Ornitz D M. Receptor specificity of the fibroblast growth factor family. The complete mammalian FGF family. *J Biol Chem*. Jun. 9, 2006; 281(23):15694-15700). FGF1 functions to regulate the endothelial cell migration and proliferation, and is involved in angiogenesis (see Wang W P, Lehtoma K, Varban M L, Krishnan I, Chiu I M. Cloning of the gene coding for human class 1 heparin-binding growth factor and its expression in fetal tissues. *Mol Cell Biol*. June 1989; 9(6):2387-2395; Chen G J, Forough R. Fibroblast growth factors, fibroblast growth factor receptors, diseases, and drugs. *Recent Pat Cardiovasc Drug Discov*. June 2006; 1(2):211-224).

The functions of FGF1 in neural tissues including brain and retina have been well characterized (Wang W P, Lehtoma K, Varban M L, Krishnan I, Chiu I M. Cloning of the gene coding for human class 1 heparin-binding growth factor and its expression in fetal tissues. *Mol Cell Biol*. June 1989; 9(6):2387-2395; Catalani E, Tomassini S, Dal Monte M, Bosco L, Casini G. Localization patterns of fibroblast growth factor 1 and its receptors FGFR1 and FGFR2 in postnatal mouse retina. *Cell Tissue Res*. June 2009; 336(3):423-438; Basilico C, Moscatelli D. The FGF family of growth factors and oncogenes. *Adv Cancer Res*. 1992; 59:115-165; Dono R. Fibroblast growth factors as regulators of central nervous system development and function. *Am J Physiol Regul Integr Comp Physiol*. April 2003; 284(4):R867-881). FGF-1 acts as a mitogen for neuroectoderm-derived cells by sustaining neural stem cell growth and self-renewal capacity in vitro (see Lee D C, Hsu Y C, Chung Y F, et al. Isolation of neural stem/progenitor cells by using EGF/FGF1 and FGF1B promoter-driven green fluorescence from embryonic and adult mouse brains. *Mol Cell Neurosci*. May 3, 2009; Nurcombe V, Ford M D, Wildschut J A, Bartlett P F. Developmental regulation of neural response to FGF1 and FGF2 by heparan sulfate proteoglycan. *Science*. Apr. 2, 1993; 260(5104):103-106; Bartlett P F, Brooker G J, Faux C H, et al. Regulation of neural stem cell differentiation in the forebrain. *Immunol Cell Biol*. October 1998; 76(5):414-418). Mitogenic effect and modulation of differentiation by FGF1 was also observed in tissues of mesoderm lineage (Jacob A L, Smith C, Partanen J, Ornitz D M. Fibroblast growth factor receptor 1 signaling in the osteo-chondrogenic cell lineage regulates sequential steps of osteoblast maturation. *Dev Biol*. Aug. 15, 2006; 296(2):315-328; Fu Y M, Spirito P, Yu Z X, et al. Acidic fibroblast growth factor in the developing rat embryo. *J. Cell Biol*. September 1991; 114(6):1261-1273; Grunz H, McKeehan W L, Knochel W, Born J, Tiedemann H. Induction of mesodermal tissues by acidic and basic heparin binding growth factors. *Cell Differ*. February 1988; 22(3):183-189).

The human FGF1 gene contains three protein-coding exons and a long 3-untranslated region that the whole gene spans over 120-kb. Four upstream untranslated exons, designated as 1A, 1B, 1C, and 1D, which are resulted from distinct transcriptional start sites (TSSs) in FGF1 promoter have been identified and these alternative promoters direct the tissue-specific expression of FGF1 (Payson R A, Canatan H, Chotani M A, et al. Cloning of two novel forms of human acidic fibroblast growth factor (aFGF) mRNA. *Nucleic Acids Res*. Feb. 11, 1993; 21(3):489-495; Myers R L, Payson R A, Chotani M A, Deaven L L, Chiu I M. Gene structure and differential expression of acidic fibroblast growth factor mRNA: identification and distribution of four different transcripts. *Oncogene*. February 1993; 8(2):341-349; Myers R L, Chedid M, Tronick S R, Chiu I M. Different fibroblast growth factor 1 (FGF1) transcripts in neural tissues, glioblastomas and kidney carcinoma cell lines. *Oncogene*. Aug. 17, 1995; 11(4): 785-789).

FGF1B (F1B) is the major transcript within the human brain and retina (Myers R L, Ray S K, Eldridge R, Chotani M A, Chiu I M. Functional characterization of the brain-specific FGF1 promoter, FGF-1.B. *J Biol Chem*. Apr. 7, 1995; 270 (14):8257-8266) while -1A transcript predominates in kidney (Myers R L, Payson R A, Chotani M A, Deaven L L, Chiu I M. Gene structure and differential expression of acidic fibroblast growth factor mRNA: identification and distribution of four different transcripts. *Oncogene*. February 1993; 8(2):341-349), and -1C and -1D transcripts predominate in vascular smooth muscle cells and fibroblasts (Chotani M A, Payson R L, Winkles J A, Chiu I M. Human fibroblast growth factor 1 gene expression in vascular smooth muscle cells is modulated via an alternate promoter in response to serum and phorbol ester. *Nucleic Acids Res*. Feb. 11, 1995; 23(3):434-441). The expression of F1B mRNA is restricted to the sensory and motor nuclei in the brain stem, spinal cord, and other areas that are known to be abundant for NSPCs (Alam K Y, Frostholm A, Hackshaw K V, Evans J E, Rotter A, Chiu I M. Characterization of the 1B promoter of fibroblast growth factor 1 and its expression in the adult and developing mouse brain. *J Biol Chem*. Nov. 22, 1996; 271(47):30263-30271).

Transgenic mouse in which an SV40 T antigen (Tag) was placed under the control of F1B promoter resulted high incidence of tumors in olfactory bulb, ventral forebrain, subventricular zone, thalamus, striatum, and tegmental area (Chiu I M, Touhalisky K, Liu Y, Yates A, Frostholm A. Tumorigenesis in transgenic mice in which the SV40 T antigen is driven by the brain-specific FGF1 promoter. *Oncogene*. Dec. 14, 2000; 19(54):6229-6239; Weiss W A, Israel M, Cobbs C, et al. Neuropathology of genetically engineered mice: consensus report and recommendations from an international forum. *Oncogene*. Oct. 24, 2002; 21(49):7453-7463). Transgenic GFP expression using F1B promoter driven vector facilitate isolation of GFP positive neural stem/progenitor cells from the developing and adult mouse brain tissue (Lee D C, Hsu Y C, Chung Y F, et al. Isolation of neural stem/progenitor cells by using EGF/FGF1 and FGF1B promoter-driven green fluorescence from embryonic and adult mouse brains. *Mol Cell Neurosci*. May 3, 2009; Hsu Y C, Lee D C, Chen S L, et al. Brain-specific 1B promoter of FGF1 gene facilitates the isolation of neural stem/progenitor cells with self-renewal and multipotent capacities. *Dev Dyn*. February 2009; 238(2):302-314). Limited by the depth resolution and penetrating ability associated with green fluorescence protein, F1B-GFP mouse was not able to demonstrate the whole body distribution of GFP to reflect the F1B promoter activity in vivo.

However, the transgenic mouse model with tissue-specific trimodality reporter expression has not been described yet.

SUMMARY OF THE INVENTION

The present invention relates to a novel F1B-TMIR (trimodal imaging reporter gene) plasmid vector comprising a nucleotide sequence of human FGF1B promoter and reporter genes for expressing bioluminescence, fluorescence, and nuclear medical imaging in live mammals. In particular, the F1B-TMIR plasmid vector possesses the DNA sequence as set forth in SEQ ID NO: 1, and expresses firefly luciferase, eGFP, and HSV1tk specific nuclear medical imaging.

Further, the present invention provides a novel transgenic mammal whose genome comprises a nucleotide sequence of human FGF1B promoter and trimodal imaging reporter genes for expressing bioluminescence, fluorescence, and nuclear medical imaging, in particular, for expressing firefly luciferase, eGFP, and HSV1tk specific nuclear medical imaging.

The present invention also provides a novel transgenic mammal whose genome comprises F1B-TMIR plasmid DNA as set forth in SEQ ID NO: 1 including nucleotide sequence of human FGF1B promoter and nucleotide sequences encoding the firefly luciferase, eGFP, and HSV1tk.

In addition, the present invention provides a method for detecting the visualizing cell-dynamic processes in vivo in a longitudinal study, which comprises (1) providing a transgenic mammal whose genome comprises a tissue-specific gene as F1B-TMIR plasmid vector, and (2) detecting the tissue-specific gene expression in that transgenic mammal by using suitable imaging platforms.

The present invention further provides a F1B-TMIR mouse mesenchymal stem cells as donor tissues in tissue engineering application and in cell therapy, which is obtained from the transgenic mammal whose genome comprises the F1B-TMIR plasmid vector. F1B-TMIR labeled cells can be applied in the study or therapy of neurodegenerative diseases and diseases with bone/ligament implications such as but not limited to osteoporosis and arthritis.

By using TMIR as reporter, the examination of in vivo FGF1B promoter activity by detecting temporal and tissue specific expression of TMIR reporter genes in transgenic mammal is achievable, it can help to elucidate novel functions and roles of FGF1. It is suggested that the role of FGF1 in the development and maturation of neural and skeletal systems. Transgenic TMIR expression greatly facilitates in vivo multimodal imaging and allows efficient and non-invasive analysis for endogenous promoters.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 7A-B. SEQ ID NO 1.

DESCRIPTION OF EMBODIMENTS OF THE INVENTION

Figure 1A:
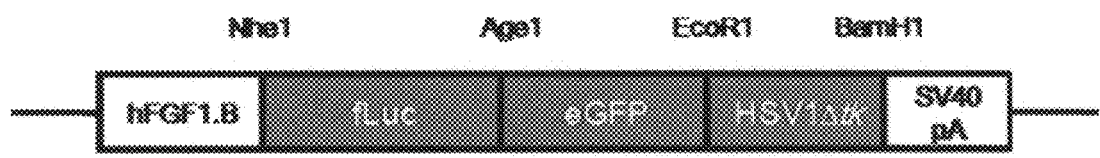
FIG. 1. (A) Structure of the F1B-TMIR transgenic vector. The restriction sites mentioned in the construction method are shown. (B) Fluorescent pictures of CHO cells transiently transfected by F1B-TMIR vector. Scale bar=100 µm. (C) The luciferase activity in FIB-TMIR transfected CHO cells following the incubation with GCV. The data shown were the luciferase activity normalized to the β-gal activity from a co-transfected RSV-β-gal vector. Error bars represent mean+SEM, n=3, *$P<0.05$, compared to the untreated group.

In one aspect, the present invention provides a novel, trimodal imaging reporter vector that contains reporter genes for fluorescence, bioluminescence, and nuclear medical imaging, driven by FGF1B promoter. In one embodiment, the F1B-TMIR plasmid vector possesses the DNA sequence as set forth in SEQ ID NO: 1, and expresses firefly luciferase, eGFP, and HSV1tk specific nuclear medical imaging.

In another aspect, the present invention provides a transgenic mammal, preferably a transgenic rodent. Incorporated into the genome of the transgenic mammal is the F1B-TMIR plasmid vector which comprises a promoter comprising an active portion of the FGF1B promoter. Operably linked to the promoter is a reporter gene, i.e., DNA fragment, comprising a sequence encoding the firefly luciferase, eGFP, and truncated HSV1tk. The term "active portion of the FGF1B promoter" as used herein refers to the nuclear factor binding region of the RR2 cis acting element of the FGF1B promoter. In one embodiment the active portion is derived from the human FGF1B promoter and comprises nucleotides 1-577 of SEQ ID NO. 1.

The term "mammal" as used herein refers to any non-human mammal. Such mammals are, for example, rodents, non-human primates, sheep, dogs, cows, and pigs. The preferred non-human mammals are selected from the rodent family including rat and mouse, more preferably mouse. A "transgenic mammal" as used herein refers to an animal containing one or more cells bearing genetic information, received, directly or indirectly, by deliberate genetic manipulation at the subcellular level, such as by microinjection or transfection with recombinant DNA, or infection with recombinant virus.

The transgene comprises a trimodal imaging reporter gene. As used herein the term "reporter gene" refers to a DNA fragment that encodes an assayable product. The assayable product is a protein or peptide or mRNA which permits differentiation of transformed brain cells which express such gene from cells that do not.

As used herein the term "trimodal imaging reporter gene" or "trifusion reporter plasmid" refers to a DNA fragment that comprises three reporter genes operably fused and allowing for simultaneous expression.

In one embodiment, the promoter is derived from a human and comprises nucleotides −145 to nucleotide +1, preferably nucleotide −507 through nucleotide +1, and more preferably nucleotide −540 to nucleotide +1, which is the transcription initiation site, of the human FGF1B promoter. Preferably, the promoter which is derived from FGF1B promoter of an animal further comprises nucleotides downstream from the transcription site, such as for example the 31 nucleotides of the 5'-untranslated sequence of the corresponding FGF1 gene.

In accordance with the present invention, it has been determined that a promoter comprising 540 base pairs of the human FGF1B promoter sequence and the first 31 base pairs of the 5'-untranslated sequence of the human FGF1B mRNA is particularly well-suited for expressing the transgene.

In another aspect, the present invention relates to a DNA construct comprising the transgene. Such construct is an expression vector, preferably a plasmid which allows for preparation of large amounts of the transgene. In such a plasmid, the transgene is flanked by restriction sites and the plasmid further comprises an origin of replication. Such construct may be made by cloning the promoter sequence into a vector comprising the reporter gene sequence or by cloning the reporter gene sequence into a vector comprising the promoter sequence, using conventional recombinant techniques. The DNA sequence encoding the promoter is incorporated into the construct in appropriate frame with the reporter gene sequence such that induction of the promoter causes expression of the reporter gene.

In another aspect the present invention relates to development of transgenic mammal whose genome comprise the transgene of the present invention. A DNA construct which comprises the present transgene may be integrated into the genome of the transgenic mammal by any standard method such as those described in Hogan et al., "Manipulating the Mouse Embryo", Cold Spring Harbor Laboratory Press, 1986; Kraemer et al., "Genetic Manipulation of the Early Mammalian Embryo", Cold Spring harbor Laboratory Press, 1985; Wagner et al., U.S. Pat. No. 4,873,191, Krimpenfort et al U.S. Pat. No. 5,175,384 and Krimpenfort et al., Biotechnology, 9: 88 (1991), all of which are incorporated herein by reference. Preferably, the DNA fragment is microinjected into pronuclei of zygotes of non-human mammals. These injected embryos are transplanted to the oviducts or uteri of pseudopregnant females from which founder mammals are obtained. The founder mammals (Fo), are transgenic (heterozygous) and can be mated with non-transgenic mammals of the same species to obtain F1 non-transgenic and transgenic offspring at a ratio of 1:1. A heterozygote mammal from one line of transgenic mammals may be crossed with a heterozygote mammal from a different line of transgenic mammals to produce mammals that are heterozygous at two loci. Mammals whose genome comprises the transgene are identified by standard techniques such as polymerase chain reaction or Southern assays.

Fluorescent Microscopy

The eGFP expression in F1B-TMIR or CMV-TMIR transfected cells was observed using Olympus IX71 fluorescence microscope with suitable filters. Live animal detection can be done with fluorescent stereomicroscopy or by in vivo optical imaging systems.

Bioluminescence Imaging

Bioluminescence imaging was achieved by using IVIS Imaging system 200 series (Caliper Life Sciences) established in Chang Gung Memorial Hospital, Taiwan. The animal was anesthetized with isoflurane followed by intraperitoneal injection of D-luciferin (Caliper) at 150 mg/kg. Acquiring of images for 5 min was started at 5 min post the injection of substrates and was repeated until the signal was attenuated or reached 30 min.

[$^{131}$I]-FIAU Preparation and γ-Camera Imaging

Carrier-free [$^{131}$I] (2'-fluoro-2'-deoxy-1-β-D-arabinofuranosyl-5-iodouracil) ([$^{131}$I]FIAU) was synthesized from 5-trimethylstannyl-1-(2'-deoxy-2'-fluoro-1-β-D-arabinofuranosyl)-uracil (FTAU) by an oxidative iododestannylation method as previously described (Deng W P, Yang W K, Lai W F, et al. Non-invasive in vivo imaging with radiolabelled FIAU for monitoring cancer gene therapy using herpes simplex virus type 1 thymidine kinase and ganciclovir. *Eur J Nucl Med Mol Imaging*. January 2004; 31(1):99-109). The radiochemical purity of [$^{131}$I]FIAU was >95%, as determined by thin layer chromatograph (TLC) method on a silica gel coated aluminum sheet using ethyl acetate-ethanol mixture (90:10, v/v) as the mobile phase. A Siemens E.CAM dual-head γ-camera, equipped with custom-made 1 mm pinhole collimator, was used for the animal γ-imaging. To block the thyroid uptake of radioiodine, mice were injected with sodium iodine saline (0.9% sodium iodine in normal saline, 1 ml/animal) 15 min prior to the intraperitoneal injection of 11.1 MBq [$^{131}$I] FIAU. The animal was laid in the prone position and 4 cm distant from the pinhole center to provide a full coverage of the body. The mice were anesthetized using isoflurane and kept warming under a tungsten lamp during injection and scan period. The image was scanned one week after injection of probe to ensure adequate clearance of unwanted background radioactivity. Static images for 30 min, using a 128× 128 matrix size and zoom 2, was collected for each animal.

Although we have used [$^{131}$I]FIAU herein, other tracers include deoxythymidine, or analogues such as stavudine, idoxuridine, aciclovir, azidothymidine (AZT), and derivatives thereof. Acycloguanosines [e.g. acyclovir, ganciclovir (GCV), penciclovir (PCV)], and the acycloguanosine derivative [e.g. 9-(4-fluoro-3-[hydroxymethyl]butyl)guanine (FHBG), 9-[(3-fluoro-1-hydroxy-2-propoxy)methyl]guanine (FHPG)], and 2'-fluoro-nucleoside analogues of thymidine [e.g. 5-iodo-2'-fluoro-2' deoxy-1-β-D-arabino-furanosyluracil (FIAU) and 2'-deoxy-2'-18F-fluoro-5-ethyl-1-β-D-arabinofuranosyl-uracil (FEAU)] are also among the bases that can be radio labeled for use in the invention. Radio labels include $^{131}$I, $^{124}$I, $^{125}$I, $^{18}$F, $^{11}$C, $^{14}$C, $^{3}$H, $^{76}$BR and the like. Further, we have used a gamma camera for imaging, but any Positron emission tomography (PET), Computed tomography (CT), High Resolution CT (HRCT) or other imaging methods, such as single photon emission computed tomography (SPECT), or PET-CT, SPECT-CT hybrid systems, and the like can be used.

Immunohistochemistry

Paraffin embedded tissue section (5 μm) was stained with rabbit anti-firefly luciferase antibody (Santa Cruz) followed by staining with Alexa488-conjugated secondary antibody. The slides were counterstained with DAPI for nucleus staining.

Mesenchymal Stem Cell Isolation and Differentiation

After euthanized by $CO_2$, gonadal fat pads of the F1B-TMIR mouse were isolated and digested according to the previous published protocol with minor modifications (Yamamoto N, Akamatsu H, Hasegawa S, Yamada T, Nakata S, Ohkuma M, Miyachi E, Marunouchi T, Matsunaga K (2007). Isolation of multipotent stem cells from mouse adipose tissue. *J Dermatol Sci*. 48, 43-52).

The isolated SVF were immediately plated for experiment or cryopreserved for future studies. SVF were cultured in αMEM supplemented with 10% fetal bovine serum and 1% penicillin—streptomycin at humidified incubator kept at 37° C. with 5% $CO_2$. Medium was changed after 72 hr to select adherent cells and every 3 days thereafter.

Osteogenic Induction, Alizarin Red and Von Kossa Stain

Osteogenic differentiation was induced by feeding ADSCs twice a week for 21 days with osteogenic induction medium consisting of 100 nM dexamethasone, 10 mM glycerophosphate, 0.05 mM ascorbic acid 2-phsophate (Fluka) and 10% FCS in αMEM. For negative controls, cells were kept in regular medium. The degree of osteogenic differentiation is by Alizarin Red and Von Kossa stain for $Ca^{2+}$ deposition by following previously described protocol.

Myogenic Induction and Liu's Stain

Subconfluent cells were differentiated by treatment with 10 μM of 5-azacytidine for 21 days. Myocyte lineage differentiation was examined by Liu's stain for myotube fusions.

Adipogenic Induction and Oil-Red-O Stain

Adipogenic differentiation was induced by adipogenic induction medium consisting of 10 μM dexamethasone, 0.25 μM 3-isobutyl-1-methyl-xanthine, 4 μM recombinant human insulin, 10 μM Troglitazone, and 10% FCS. After 21 days, adipogenic differentiation was confirmed by the formation of neutral lipid-vacuoles stainable with Oil-Red O.

Chondrogenesis Induction

Chondrogenesis differentiation was induced by chondrogenic medium consisting of 10 ng/ml TGF3, 100 nM dexamethasone, 50 μg/ml ascorbic acid, 1 mM sodium pyruvate, 6.25 μg/ml insulin, 6.25 μg/ml transferrin, 6.25 ng/ml selenous acid (ITS-Premix), 1.25 mg/ml bovine serum albumin, and 5.35 mg/ml linoleic acid in DMEM-high glucose.

The following examples are for purposes of illustration only and are not intended to limit the scope of the claims which are appended hereto.

EXAMPLES

Example 1

The Construction of Trimodal Imaging Reporter (TMIR) Vector

Tri-reporter fusion was constructed by linking in-frame coding sequences of firefly luciferase, enhanced green fluorescent protein (eGFP), and HSV1Δtk with the truncation at HSV1tk N terminus. In short, the eGFP-tk fusion vector was previously described by the present inventors (Lin K M, Hsu C H, Chang W S, Chen C T, Lee T W. Human breast tumor cells express multimodal imaging reporter genes. *Mol Imaging Biol*. September 2008; 10(5):253-263), containing HSV1tk (Gene bank:CAA23742) coding sequence (a.a. 1-376) inserted to the C-terminus of eGFP expressing vector (EGFP-C2, Clonetech) at EcoR1/BamH1 sites. The first 135 by of HSV1tk in eGFP-tk was removed by PCR method and resulted in the eGFP-Δtk which driven by CMV promoter. 540 by of ApaL1/Age1 F1B promoter fragment was isolated from F1B-GFP vector (Lee D C, Hsu Y C, Chung Y F, et al. Isolation of neural stem/progenitor cells by using EGF/FGF1 and FGF1B promoter-driven green fluorescence from embryonic and adult mouse brains. *Mol Cell Neurosci*. May 3, 2009; Hsu Y C, Lee D C, Chen S L, et al. Brain-specific 1B promoter of FGF1 gene facilitates the isolation of neural stem/progenitor cells with self-renewal and multipotent capacities. *Dev Dyn*. February 2009; 238(2):302-314) and cloned into eGFP-Δtk to replace the CMV promoter and resulted in F1B-eGFP-Δtk. The firefly luciferase coding sequence (Luc) was isolated from pGL2 vector (Promega) by PCR using primers containing Age1 sites and the resultant fragment was cloned into the F1B-eGFP-Δtk to receive F1B-Luc-eGFP-Δtk (F1B-TMIR)

vector. Similarly, Luc was inserted into eGFP-Δtk to receive CMV-TMIR. All vectors were verified by DNA sequencing.

Example 2

Cell Culture, Transfection, Ganciclovir (GCV) Treatment, and Luciferase Activity Assay Chinese hamster ovary cancer cells (CHO-K1) were maintained in F-12 medium supplemented with 10% fetal bovine serum (FBS) and the antibiotics penicillin, streptomycin, and amophotericin B (PSA) in a 95% air and 5% $CO_2$ humidified incubator. DNA vectors including a RSV β-galactosidase control vector for normalization of transfection efficiency were transfected into the cells using PolyFect (Qiagen) reagent by following manufacturer's protocol. 16 h after transfection, the cells were treated with GCV at the indicated concentrations and incubated for 72 h, followed by the cell lysis, luciferase and β-gal activity assay using a luciferase/β-gal assay kit (Promega).

Example 3

Animal Studies

All animal experiments were conducted in accordance with accepted standards of animal care and were approved by the Institutional Animal Care and Use Committee of the National Health Research Institutes, Taiwan. FVB/NarL transgenic mice were generated in the Level Biotech Inc. (Taipei, Taiwan) using ApaL1/PvuII digested F1B-TMIR vector. A total of 6 transgenic founders were generated and transgenic lines from four of the founders (#2, #7, #29, and #49) were subsequently analyzed. The genotyping of transgene positive mice was performed by PCR using the primers TTGACCGGTCACCATGGAAGACGCCAAA (SEQ ID NO. 2) and CGTCGCCGTCCAGCTCGACCAG (SEQ ID NO. 3) to amplify the transgene. Southern blotting of transgenic mice was performed on mouse tail DNA digested by NcoI followed by 0.8% agarose electrophoresis and transfer to nylon membrane. Full length eGFP cDNA was labeled by $^{32}P$-αdCTP and used as the probe to detect transgenes. As the structure of F1B-TMIR shown in FIG. 1A, Nco1 digestion could result in 3.6 kb band in the blot from the head-to-tail arrangement of transgenes or in a 5.2 kb band representing a tail-to-tail arrangement of transgene.

Example 4

In Vitro Functional Testing of CMV-TMIR and F1B-TMIR

Figure 1B:
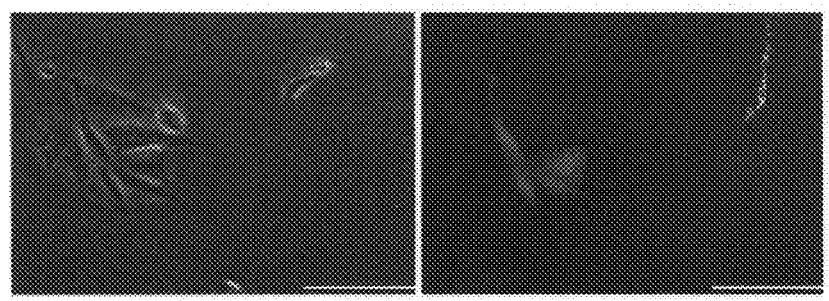
Figure 1C:
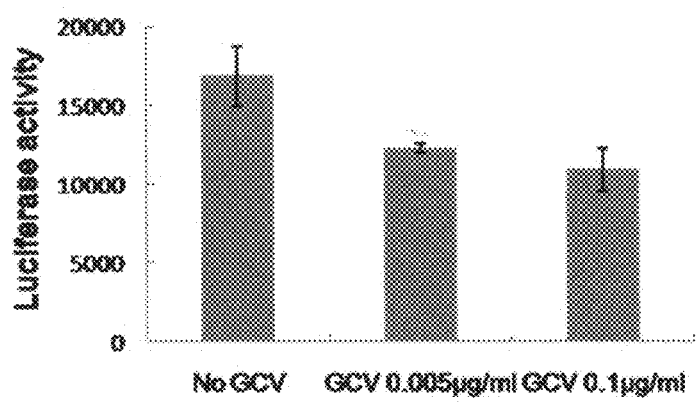

The TMIR vectors driven by CMV or F1B promoter were constructed as foregoing description. Transfection of these two vectors into CHO cells resulted in green fluorescence primarily in the cytoplasm, indicating that the removal of N-terminal residue of HSV1tk resulted in preferred cytoplasm localization of fusion protein, compared to the eGFP-tk fusion protein that was primarily localized in nucleus (Deng W P, Yang W K, Lai W F, et al. Non-invasive in vivo imaging with radiolabelled FIAU for monitoring cancer gene therapy using herpes simplex virus type 1 thymidine kinase and ganciclovir. *Eur J Nucl Med Mol Imaging*. January 2004; 31(1): 99-109). There was a decrease in the number of cells expressing GFP and in the intensitity of fluorescence in F1B-TMIR transfected cells than cells transfected by CMV-TMIR (FIG. 1B) as a result of weaker transactivity by F1B promoter. Previously, we have shown that the $ED_{50}$ (the dose resulted in 50% of cell death after 7 days) by GCV to MDA-MB231 cells that constitutively express large amount of eGFP-tk to be 0.005 μg/ml, and the $ED_{50}$ to ZR75-1 cells that constitutvely express low amount of the same reporter to be around 0.1 μg/ml (Deng W P, Yang W K, Lai W F, et al. Non-invasive in vivo imaging with radiolabelled FIAU for monitoring cancer gene therapy using herpes simplex virus type 1 thymidine kinase and ganciclovir. *Eur J Nucl Med Mol Imaging*. January 2004; 31(1):99-109). Thus, TMIR vector-transfected CHO cells were either treated by 0.005 μg/ml or 0.1 μg/ml GCV for 72 h or were treated only by vehicles, followed by the luciferase and β-gal activity assays. As the result shown in FIG. 1 C, transfection by F1B-TMIR in CHO cells resulted in 20-fold less luciferase activity than that by CMV-TMIR, indicating functional luciferase activity in TMIR fusion reporting weak F1B promoter activation. The sensitivity to GCV was used as the indication for functioning HSV1Δtk in transfected cells. Indeed, treatment with low or high concentration of GCV results in 35% loss of luciferase activity in F1B-TMIR transfected cells and 45% loss of activity in CMV-TMIR transfected cells. Thus, HSV1Δtk in TMIR fusion was functionally able to mediate the GCV-induced cell death when expressed in cells.

Example 5

Distribution of Tri-Reporter in F1B-TMIR Tg Mouse

Figure 2:
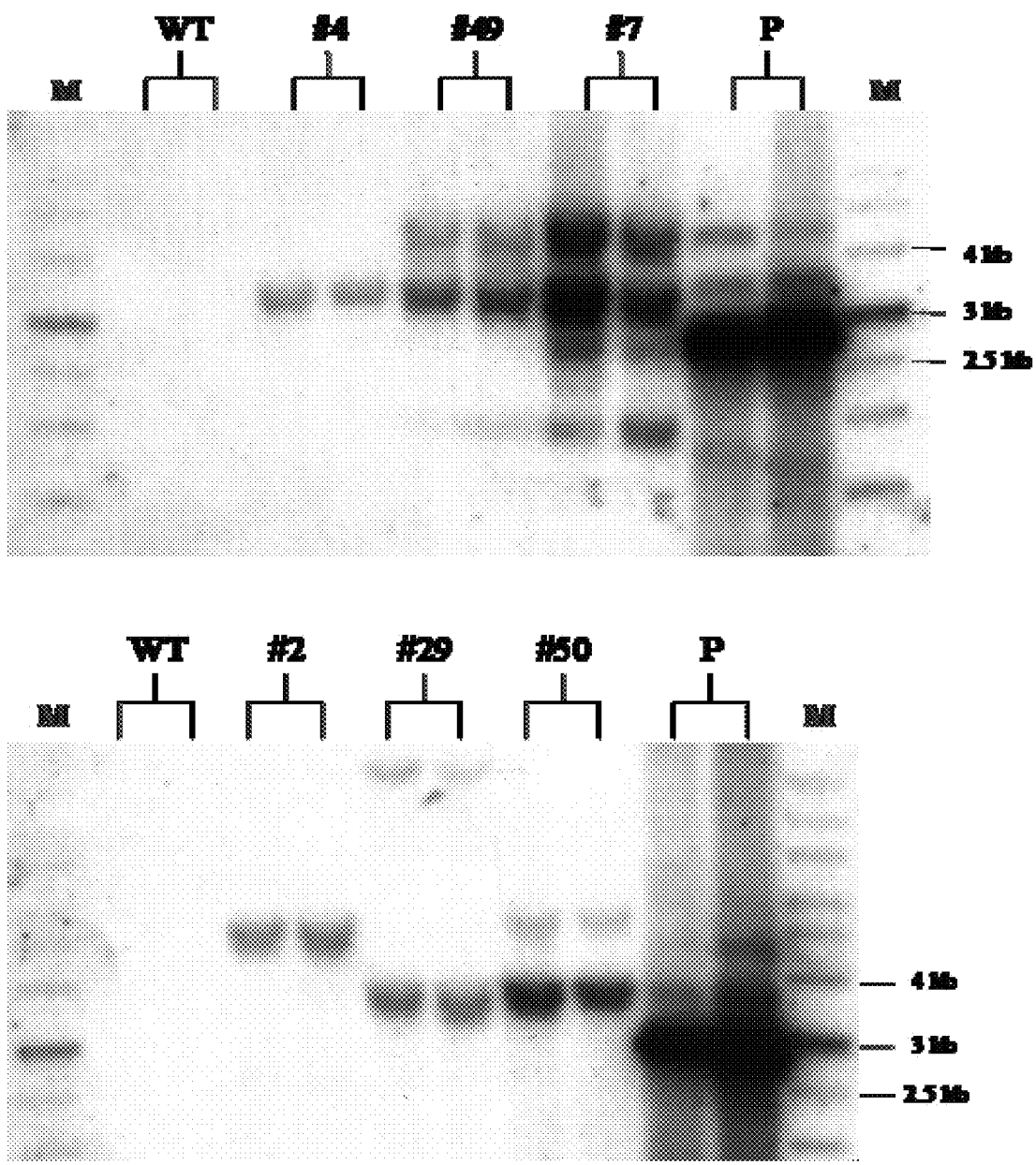
FIG. 2. Southern blotting of different lines of F1B-TMIR mice and the lines #2, #7, #29, #49 were used in this study. Marker (M) and 100 pg of F1B-TMIR vector (P) loaded as the positive control are shown.

Total 6 transgenic lines of F1B-TMIR were generated and the southern blotting of 5 of the 6 lines are shown in FIG. 2. Line #4 contains only one or few transgene copies, resulting in undetectable level of signals by bioluminescent imaging (data not shown). Therefore we analyzed four other lines representing mice containing medium (#2, #29, #49, 2-5 copies), and high transgenic copies (#7, 10-20 copies). With the instruments available to us, the green fluorescence in isolated organs or of the whole body was not distinguished from autofluorescence presented in tissues, therefore, in vivo observation of TMIR expression was relied on bioluminescence and HSV1Δtk nuclear imaging. However, in vivo imaging can easily be achieved with more sensitive imaging equipment than is available to us (e.g., ultra-sensitive CCD cameras are commercially available), and traditional biochemical techniques such as tmmunoblotting, immunohistochemistry, and the like are also available.

Figure 3A:
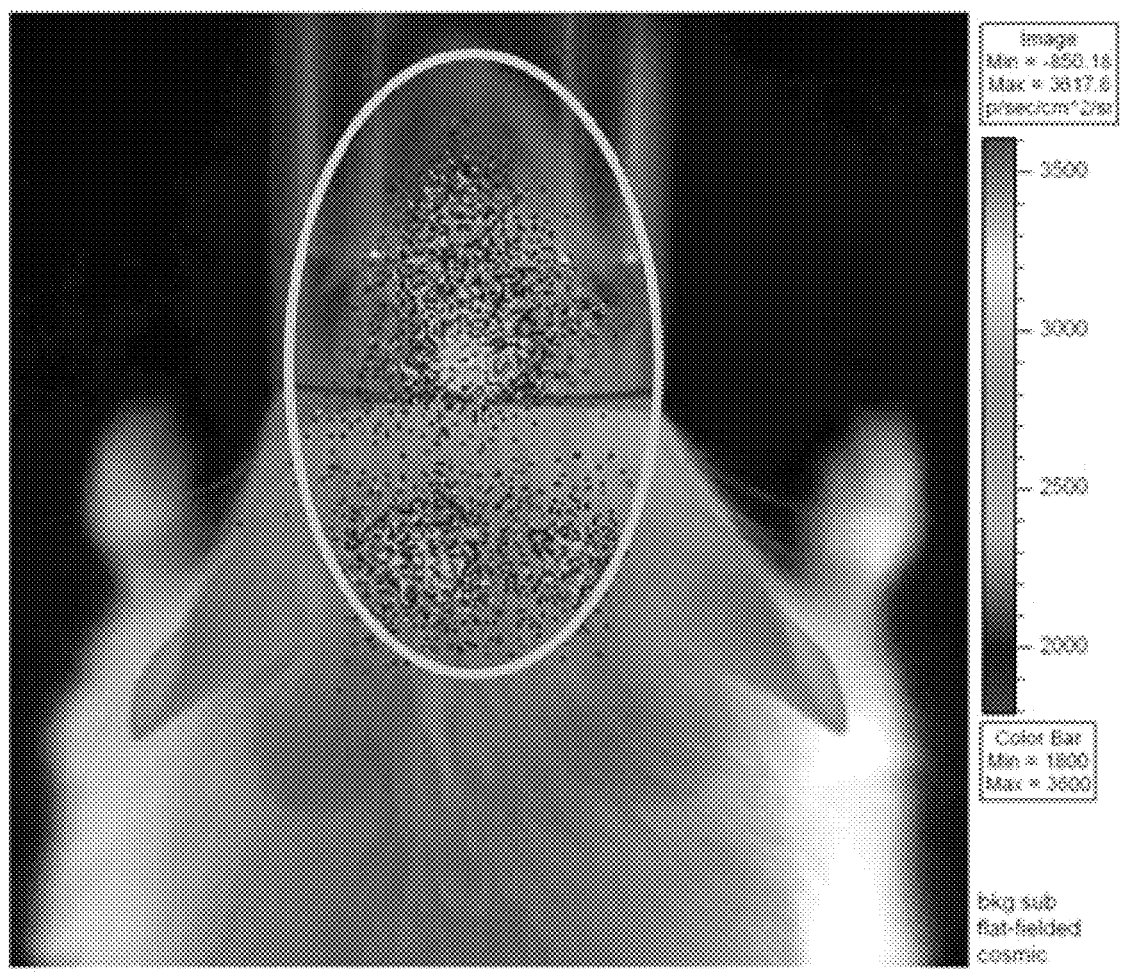
FIGS. 3A, 3B and 3C. Bioluminescent images of F1B-TMIR mice showing TMIR expression in the brain including olfactory bulb, forebrain, brain stem and other regions including turbinate, eyes, and testis.
Figure 3B:
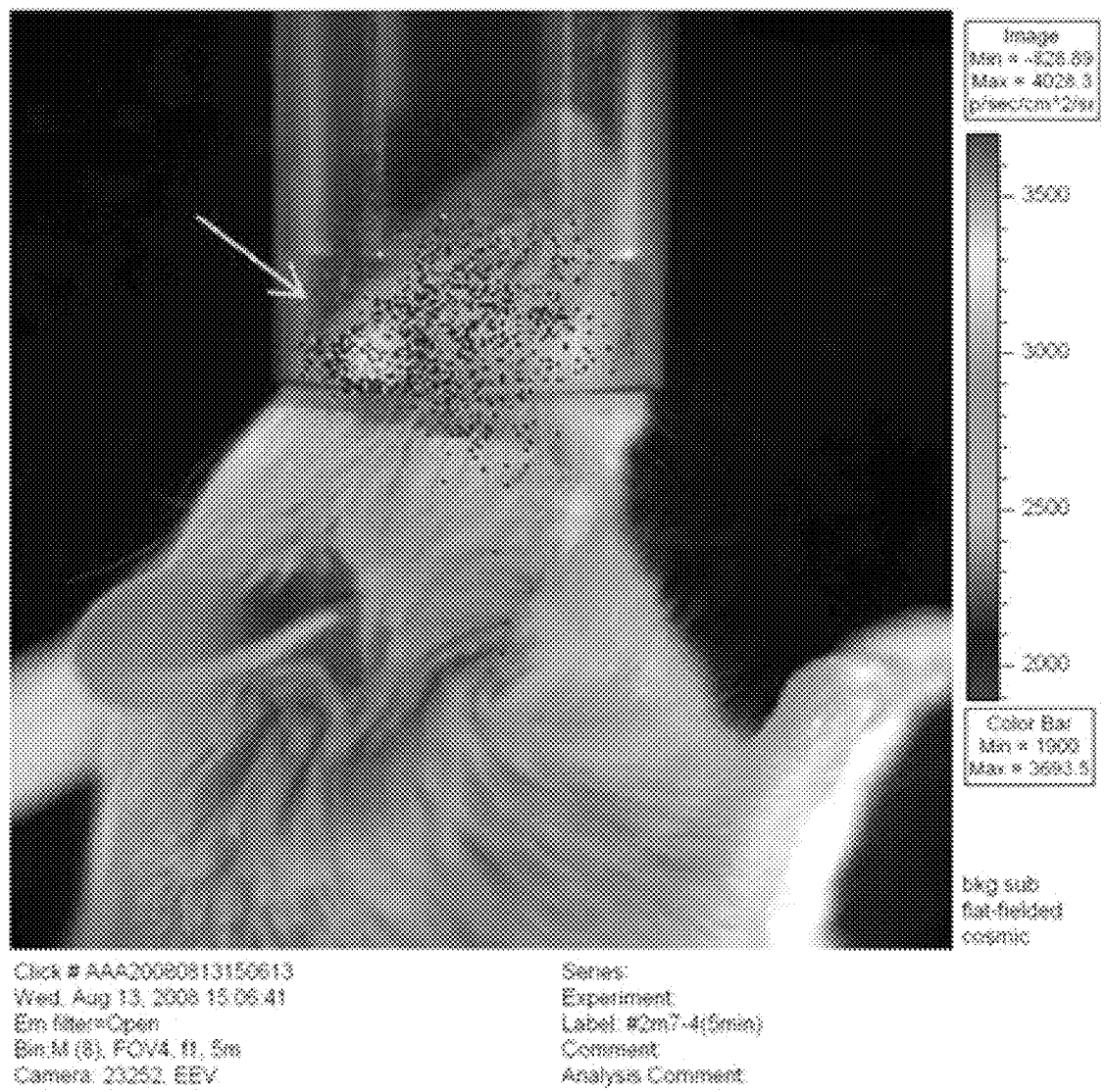
Figure 3C:
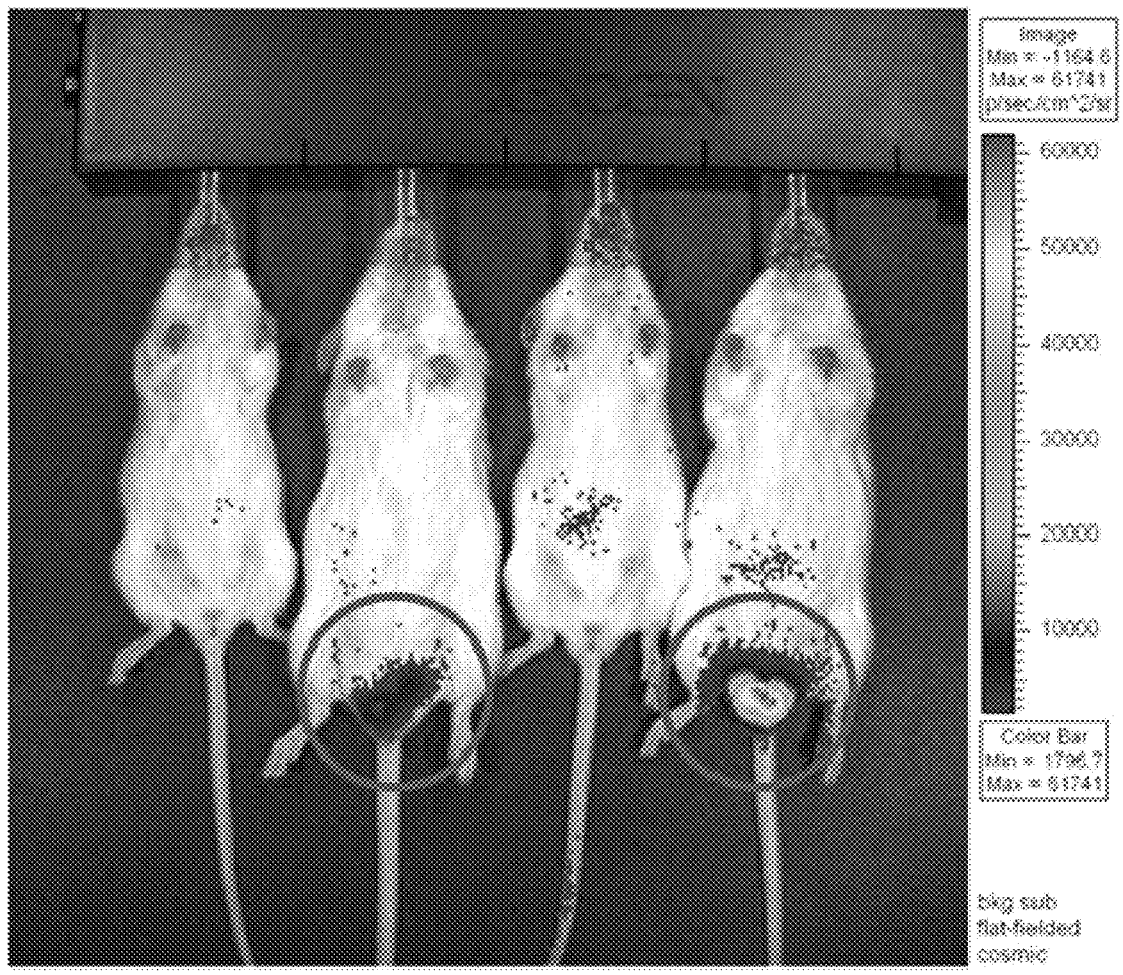
Figure 4:
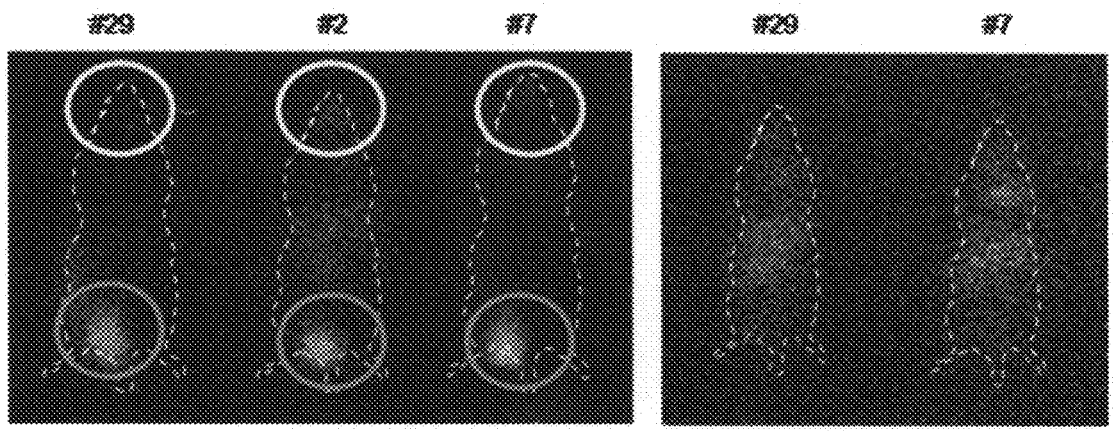
FIG. 4. [$^{131}$I]FIAU γ imaging performed on #2, #7, and #29 F1B-TMIR mice one week after probe injection (Left) reveals strong uptake in testis and low uptake at head. Image of young female mice #7, #29 (Right) was shown for comparison.

The result of bioluminescent imaging demonstrated signals that were located only in the head including olfactory bulb, turbinate, eyes, brain stem, between ears. Strong bioluminescent signals in the testis of male mouse were also observed (FIG. 3). We used [$^{131}$I]FIAU to label the TMIR expressing tissues and performed the γ-imaging one week after injecting the probes. As shown in FIG. 4, in addition to some signals at head, there was a strong uptake of [$^{131}$I]FIAU in the testis, confirmed by the absence of similar signals in female mice.

Figures 5A, 5B, 5C, 5D, 5E, 5F:
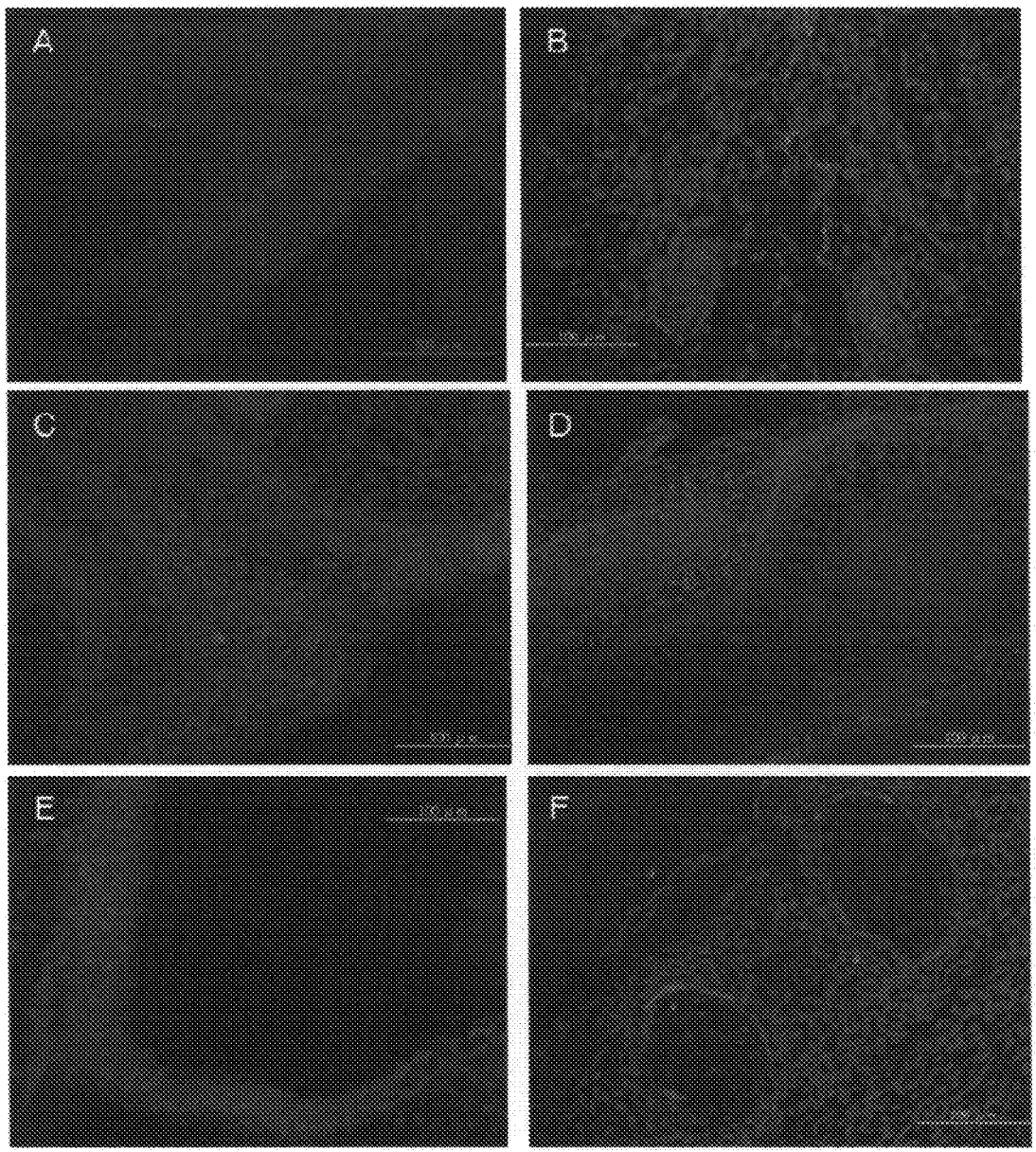
FIG. 5. Detection of luciferase expression by immunofluorescence staining using anti-luciferase antibody and Alexa Fluor 488-conjugated secondary antibody. Expression of TMIR in cerebellum brain stem (A), olfactory bulbs (B), tongue mucous membrane (C), auditory meatus (D), hyaline cartilage of naso-pharynx (E), perichondrium of the rib (F). DAPI was used to counterstain nucleuses. Scale bar=100 μm.

To detect the in situ TMIR expression microscopically, we performed the immunofluorescence detection using anti-luciferase antibody and Alexa Fluor 488-conjugated secondary antibody on paraffin embedeed sections of neonatal adult mouse. As shown in images of FIG. 5, positive detection of luciferase was found in olfactory epithelium, olfactory nerves, mucous layer of tongue, turnibate, hyaline cartilage of naso-pharynx, white matter of cerebellum, pinna and external auditory meatus of ear, perichondrium of ribs and axial skeleton. Most of above areas was also detected by in vivo imaging. The most consistant findings of TMIR expression in neonatal and adult F1B-TMIR mice are at the regions of olfactory bulb, forebrain, brain stem, turnibate, eyes, skull cartilage, and testis.

Example 6

Directed Differentiation of Mesenchymal Stem Cells in F1B-TMIR Mouse

Figure 6:
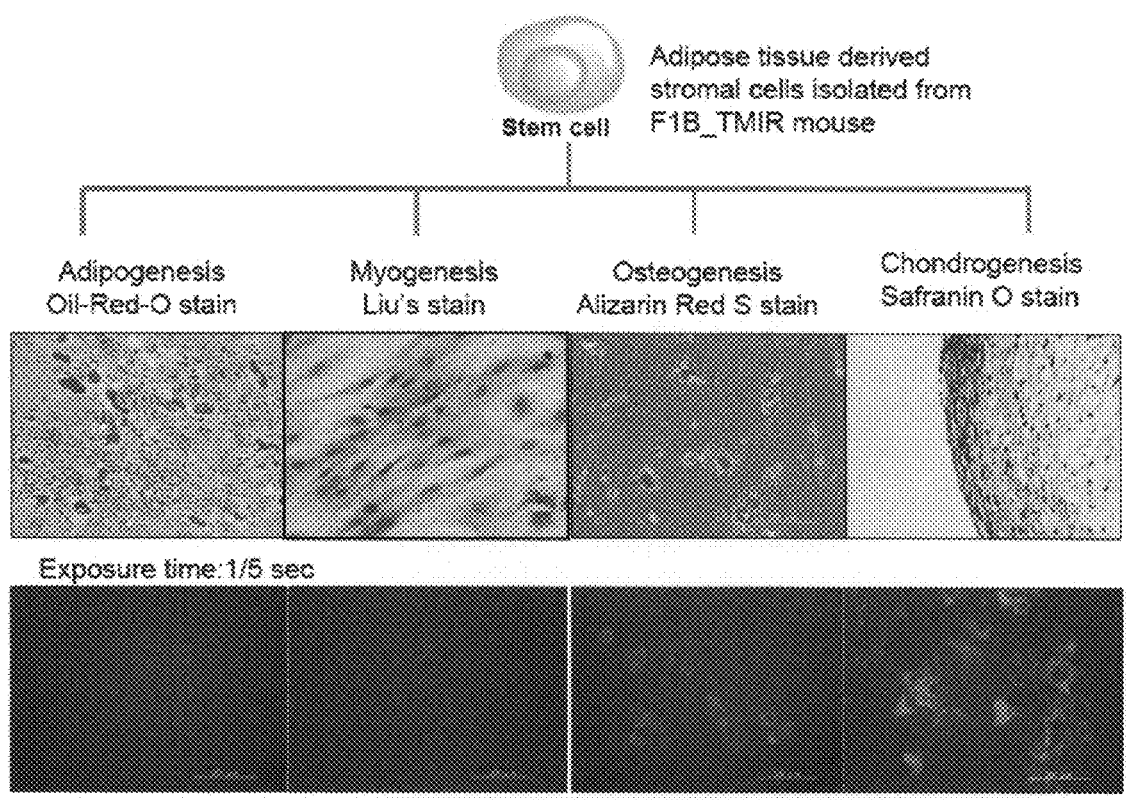
FIG. 6. Cell type specific TMIR expression in differentiated MSC isolated from F1B-TMIR.

Mesenchymal stem cells isolated from various animal tissues exhibit the pluripotency to various tissues of mesoderm lineages, including skeletal muscles, osteoblasts, adipocytes, and chondrocytes. Here, we used the mesenchymal stem cells isolated from adult adipose tissue of F1B-TMIR mice (adipose tissue derived stromal cells), and induced the differentiation toward to the above four different types of tissues. As shown in FIG. 6, osteoblasts and chondrocytes derived from F1B-TMIR express high level of GFP. In contrast, TMIR was not expressed in matured myoblasts and adipocytes differentiated from the same MSC. Thus, MSC of F1B-TMIR are those stem cells already labeled with functional TMIR that can be used as the source of stem cells used for transplantation and tracing in various diseases models including bone and ligament related diseases such as osteoporosis and arthritis.

We have demonstrate one of the first tri-reporter transgenic mice (Tong R, Ray P, Gambhir S. The universal donor mouse: a mouse expressing a tri-fusion reporter gene in all tissues. *World Molecular Imaging Conference*. Nice, France; 2008: 0911) functioning in vitro and in vivo. Driven by a relatively weak F1B promoter with the activity only in limited tissues, fluorescence imaging was not able to measure eGFP expression in vivo. Bioluminescent or nuclear imaging using HSV1tk specific probes was able to measure TMIR expression in vivo, demonstrating the superiority of these two modalities to be used in whole animal imaging. GFP in TMIR provides the opportunity to incorporate technologies developed for studies at cellular level such as fluorescence microscopy and flow cytometry. For example, the proliferation and differentiation of neural sphere/progenitor cells isolated from F1B-GFP mouse has been previously shown to be enhanced by selecting the GFP (+) cells using fluorescence activated cell sorter (Lee D C, Hsu Y C, Chung Y F, et al. Isolation of neural stem/progenitor cells by using EGF/FGF1 and FGF1B promoter-driven green fluorescence from embryonic and adult mouse brains. *Mol Cell Neurosci*. May 3, 2009., and Hsu Y C, Lee D C, Chen S L, et al. Brain-specific 1B promoter of FGF1 gene facilitates the isolation of neural stem/progenitor cells with self-renewal and multipotent capacities. *Dev Dyn*. February 2009; 238(2):302-314).

The in vivo imaging result in F1B-TMIR led us to the novel and unexpected finding of massive F1B exon expression in testis, a finding would not be perceived otherwise without in vivo TMIR imaging. The molecular basis for the activation of F1B promoter specifically in testis remains elusive and requires further investigation. Nevertheless, tri-reporter transgenic mouse like F1B-TMIR not only facilitated visualization of the specific gene expression in vivo, but also helped to find tissue- and stage-specific changes. Similar information was either difficult to acquire in the past or was only available from sources like isolated organs and in vitro cell culture models.

We report here the first tri-reporter transgenic mouse in which a trifusion reporter containing luciferase, eGFP, and HSV1Δtk is driven by a human F1B promoter. We have also developed transgenic mouse expressing such reporters. We have demonstrated the functionality of such trimodality reporter in live animals with respect to individual imaging modality. The levels of gene expression could be monitored in the same live animals repeatedly. The in vivo imaging of TMIR enabled the novel finding of mouse F1B promoter activity in testis and in the brain and proves the usefulness of applying reporter mouse technology in identifying new functions of a given gene promoter that were previously unknown. Most importantly, we have demonstrated that MSCs of F1B-TMIR are labeled with TMIR markers that selectively highly expressed when induced into osteoblasts and chondrocytes. This selectivity facilitates the use of F1B-TMIR as a tool in studies of osteogenesis and chondrogenesis.

It should be understood that the foregoing discussion and examples merely present a detailed description of certain embodiments. It therefore should be apparent to those of ordinary skill in the art that various modifications and equivalents can be made without departing from the spirit and scope of the invention All journal articles, other references, patents and patent applications that are identified in this patent application are incorporated by reference in their entirety.

REFERENCES

1. Rome C, Couillaud F, Moonen C T. Gene expression and gene therapy imaging. *Eur Radiol*. February 2007; 17(2): 305-319.
2. Kang J H, Chung J K. Molecular-genetic imaging based on reporter gene expression. *J Nucl Med*. June 2008; 49 Suppl 2:164S-179S.
3. Kesarwala A H, Prior J L, Sun J, Harpstrite S E, Sharma V, Piwnica-Worms D. Second-generation triple reporter for bioluminescence, micro-positron emission tomography, and fluorescence imaging. *Mol. Imaging*. October-December 2006; 5(4):465-474.
4. Kim Y J, Dubey P, Ray P, Gambhir S S, Witte O N. Multimodality imaging of lymphocytic migration using lentiviral-based transduction of a tri-fusion reporter gene. *Mol Imaging Biol*. September-October 2004; 6(5):331-340.
5. Ponomarev V, Doubrovin M, Serganova I, et al. A novel triple-modality reporter gene for whole-body fluorescent, bioluminescent, and nuclear noninvasive imaging. *Eur J Nucl Med Mol Imaging*. May 2004; 31(5):740-751.
6. Ray P, De A, Min J J, Tsien R Y, Gambhir S S. Imaging tri-fusion multimodality reporter gene expression in living subjects. *Cancer Res*. Feb. 15, 2004; 64(4):1323-1330.
7. Wang W P, Lehtoma K, Varban M L, Krishnan I, Chiu I M. Cloning of the gene coding for human class 1 heparin-binding growth factor and its expression in fetal tissues. *Mol Cell Biol*. June 1989; 9(6):2387-2395.
8. Miller D L, Ortega S, Bashayan O, Basch R, Basilico C. Compensation by fibroblast growth factor 1 (FGF1) does not account for the mild phenotypic defects observed in FGF2 null mice. *Mol Cell Biol*. March 2000; 20(6):2260-2268.
9. Ornitz D M, Xu J, Colvin J S, et al. Receptor specificity of the fibroblast growth factor family. *J Biol Chem*. Jun. 21, 1996; 271(25):15292-15297.
10. Zhang X, Ibrahimi O A, Olsen S K, Umemori H, Mohammadi M, Ornitz D M. Receptor specificity of the fibroblast growth factor family. The complete mammalian FGF family. *J Biol Chem*. Jun. 9, 2006; 281(23):15694-15700.
11. Chen G J, Forough R. Fibroblast growth factors, fibroblast growth factor receptors, diseases, and drugs. *Recent Pat Cardiovasc Drug Discov*. June 2006; 1(2):211-224.
12. Catalani E, Tomassini S, Dal Monte M, Bosco L, Casini G. Localization patterns of fibroblast growth factor 1 and its receptors FGFR1 and FGFR2 in postnatal mouse retina. *Cell Tissue Res.* June 2009; 336(3):423-438.
13. Basilico C, Moscatelli D. The FGF family of growth factors and oncogenes. *Adv Cancer Res.* 1992; 59:115-165.
14. Dono R. Fibroblast growth factors as regulators of central nervous system development and function. *Am J Physiol Regul Integr Comp Physiol.* April 2003; 284(4):R867-881.
15. Lee D C, Hsu Y C, Chung Y F, et al. Isolation of neural stem/progenitor cells by using EGF/FGF1 and FGF1B promoter-driven green fluorescence from embryonic and adult mouse brains. *Mol Cell Neurosci.* May 3, 2009.
16. Nurcombe V, Ford M D, Wildschut J A, Bartlett P F. Developmental regulation of neural response to FGF-1 and FGF-2 by heparan sulfate proteoglycan. *Science.* Apr. 2, 1993; 260(5104):103-106.
17. Bartlett P F, Brooker G J, Faux C H, et al. Regulation of neural stem cell differentiation in the forebrain. *Immunol Cell Biol.* October 1998; 76(5):414-418.
18. Jacob A L, Smith C, Partanen J, Ornitz D M. Fibroblast growth factor receptor 1 signaling in the osteo-chondrogenic cell lineage regulates sequential steps of osteoblast maturation. *Dev Biol.* Aug. 15, 2006; 296(2):315-328.
19. Fu Y M, Spirito P, Yu Z X, et al. Acidic fibroblast growth factor in the developing rat embryo. *J. Cell Biol.* September 1991; 114(6):1261-1273.
20. Grunz H, McKeehan W L, Knochel W, Born J, Tiedemann H. Induction of mesodermal tissues by acidic and basic heparin binding growth factors. *Cell Differ.* February 1988; 22(3):183-189.
21. Payson R A, Canatan H, Chotani M A, et al. Cloning of two novel forms of human acidic fibroblast growth factor (aFGF) mRNA. *Nucleic Acids Res.* Feb. 11, 1993; 21(3): 489-495.
22. Myers R L, Payson R A, Chotani M A, Deaven L L, Chiu I M. Gene structure and differential expression of acidic fibroblast growth factor mRNA: identification and distribution of four different transcripts. *Oncogene.* February 1993; 8(2):341-349.
23. Myers R L, Chedid M, Tronick S R, Chiu I M. Different fibroblast growth factor 1 (FGF-1) transcripts in neural tissues, glioblastomas and kidney carcinoma cell lines. *Oncogene.* Aug. 17, 1995; 11(4):785-789.
24. Myers R L, Ray S K, Eldridge R, Chotani M A, Chiu I M. Functional characterization of the brain-specific FGF-1 promoter, FGF-1.B. *J Biol Chem.* Apr. 7, 1995; 270(14): 8257-8266.
25. Chotani M A, Payson R A, Winkles J A, Chiu I M. Human fibroblast growth factor 1 gene expression in vascular smooth muscle cells is modulated via an alternate promoter in response to serum and phorbol ester. *Nucleic Acids Res.* Feb. 11, 1995; 23(3):434-441.
26. Alam K Y, Frostholm A, Hackshaw K V, Evans J E, Rotter A, Chiu I M. Characterization of the 1B promoter of fibroblast growth factor 1 and its expression in the adult and developing mouse brain. *J Biol Chem.* Nov. 22, 1996; 271(47):30263-30271.
27. Chiu I M, Touhalisky K, Liu Y, Yates A, Frostholm A. Tumorigenesis in transgenic mice in which the SV40 T antigen is driven by the brain-specific FGF1 promoter. *Oncogene.* Dec. 14, 2000; 19(54):6229-6239.
28. Weiss W A, Israel M, Cobbs C, et al. Neuropathology of genetically engineered mice: consensus report and recommendations from an international forum. *Oncogene.* Oct. 24, 2002; 21(49):7453-7463.
29. Hsu Y C, Lee D C, Chen S L, et al. Brain-specific 1B promoter of FGF1 gene facilitates the isolation of neural stem/progenitor cells with self-renewal and multipotent capacities. *Dev Dyn.* February 2009; 238(2):302-314.
30. Lin K M, Hsu C H, Chang W S, Chen C T, Lee T W. Human breast tumor cells express multimodal imaging reporter genes. *Mol Imaging Biol.* September 2008; 10(5): 253-263.
31. Deng W P, Yang W K, Lai W F, et al. Non-invasive in vivo imaging with radiolabelled FIAU for monitoring cancer gene therapy using herpes simplex virus type 1 thymidine kinase and ganciclovir. *Eur J Nucl Med Mol Imaging.* January 2004; 31(1):99-109.
32. Roura S, Farre J, Soler-Botija C, et al. Effect of aging on the pluripotential capacity of human CD105+ mesenchymal stem cells. *Eur J Heart Fail.* October 2006; 8(6):555-563.
33. Schaffler A, Buchler C. Concise review: adipose tissue-derived stromal cells—basic and clinical implications for novel cell-based therapies. *Stem Cells.* April 2007; 25(4): 818-827.
34. Tong R, Ray P, Gambhir S. The universal donor mouse: a mouse expressing a tri-fusion reporter gene in all tissues. *World Molecular Imaging Conference.* Nice, France; 2008:0911.
35. Ser. Nos. 11/375,889, 10/829,491, U.S. Pat. No. 7,045, 678, U.S. Pat. No. 6,984,518, U.S. Pat. No. 4,873,191 and U.S. Pat. No. 5,175,384.

What is claimed is:

1. A trifusion reporter plasmid comprising the sequence of SEQ ID NO: 1.

\* \* \* \* \*

SEQUENCE LISTING

```
<160> NUMBER OF SEQ ID NOS: 3

<210> SEQ ID NO 1
<211> LENGTH: 4075
<212> TYPE: DNA
<213> ORGANISM: Artificial Sequence
<220> FEATURE:
<223> OTHER INFORMATION: A trimodality imaging reporter gene that
      containing reporter genes for fluorescence, bioluminescence, and
      nuclear medical imaging, driven by FGF1.B promoter.
<220> FEATURE:
<221> NAME/KEY: Human FGF1.B promoter
<222> LOCATION: (1)..(577)
<220> FEATURE:
<221> NAME/KEY: Linker and cloning vector pEGFP-N sequence
<222> LOCATION: (578)..(640)
<220> FEATURE:
<221> NAME/KEY: TMIR coding sequence
```

```
<222> LOCATION: (641)..(4075)
<220> FEATURE:
<221> NAME/KEY: Firefly luciferase
<222> LOCATION: (641)..(2293)
<220> FEATURE:
<221> NAME/KEY: Linker
<222> LOCATION: (2294)..(2305)
<220> FEATURE:
<221> NAME/KEY: EGFP coding sequence and MCS in pEGFP-C2
<222> LOCATION: (2306)..(3061)
<220> FEATURE:
<221> NAME/KEY: Truncated human herpes simplex virus type 1 thymidine
      kinase
<222> LOCATION: (3061)..(4075)

<400> SEQUENCE: 1
gggaggtccc tttcatccag cagccttctg actccagagg agagtctccg agccacgacc      60
tgctgtttcc ctggcaactc aggcctcaaa ataaacagga ttctgctcag acgggccaga     120
agtccattcg gctcacacat ttgccccaag acaaaccacg ttaaaataac acccagggta     180
gctgctgcca ccgtcttctg tctctaccte cctcctgget ggccaatggc tctgtgttcc     240
tgggcctgct gctggctgtc cagagtaggg gttgcttaga gctgtgtgca tccctgcggg     300
tggtgtggga gtgggcggtt gtctaaaggc aggtccccte tactgataaa caaggaccgg     360
agatagacct agaggctgac attcttgget ccccagcet acaccccccc cacctcgatt     420
tcccacagag ccctagggac gggtagccag ctctgtggca tggtatctgg aggcaggcca     480
gcaacctgat gtgcatgcca cggcccgtcc ctctccccac tcagagctgc agtagcctgg     540
aggttcagag agccgggcta ctctgagaag aagacacgat ctaagtaagc ttcgaattct     600
gcagtcgacg gtaccgcggg cccgggatcc accggtcacc atggaagacg ccaaaaacat     660
aaagaaaggc ccggcgccat tctatcctct agaggatgga accgctggag agcaactgca     720
taaggctatg aagagatacg ccctggttcc tggaacaatt gcttttacag atgcacatat     780
cgaggtgaac atcacgtacg cggaatactt cgaaatgtcc gttcggttgg cagaagctat     840
gaaacgatat gggctgaata caaatcacag aatcgtcgta tgcagtgaaa actctcttca     900
attctttatg ccggtgttgg gcgcgttatt tatcggagtt gcagttgcgc ccgcgaacga     960
catttataat gaacgtgaat tgctcaacag tatgaacatt tcgcagccta ccgtagtgtt    1020
tgtttccaaa aaggggttgc aaaaaatttt gaacgtgcaa aaaaaattac caataatcca    1080
gaaaattatt atcatggatt ctaaaacgga ttaccaggga tttcagtcga tgtacacgtt    1140
cgtcacatct catctacctc ccggttttaa tgaatacgat tttgtaccag agtcctttga    1200
tcgtgacaaa acaattgcac tgataatgaa ttcctctgga tctactgggt tacctaaggg    1260
tgtggcccct ccgcatagaa ctgcctgcgt cagattctcg catgccagag atcctatttt    1320
tggcaatcaa atcattccgg atactgcgat tttaagtgtt gttccattcc atcacggttt    1380
tggaatgttt actacactcg gatatttgat atgtggattt cgagtcgtct taatgtatag    1440
atttgaagaa gagctgtttt tacgatccct tcaggattac aaaattcaaa gtgcgttgct    1500
agtaccaacc ctattttcat tcttcgccaa aagcactctg attgacaaat acgatttatc    1560
taatttacac gaaattgctt ctgggggcgc acctctttcg aaagaagtcg ggaagcggt    1620
tgcaaaacgc ttccatcttc cagggatacg acaaggatat gggctcactg agactacatc    1680
agctattctg attacacccg aggggggatga taaaccgggc gcggtcggta agttgttcc    1740
attttttgaa gcgaaggttg tggatctgga taccgggaaa acgctgggcg ttaatcagag    1800
aggcgaatta tgtgtcagag gacctatgat tatgtccggt tatgtaaaca atccggaagc    1860
gaccaacgcc ttgattgaca aggatggatg gctacattct ggagacatag cttactggga    1920
```

-continued

```
cgaagacgaa cacttcttca tagttgaccg cttgaagtct ttaattaaat acaaaggata    1980
tcaggtggcc cccgctgaat tggaatcgat attgttacaa caccccaaca tcttcgacgc    2040
gggcgtggca ggtcttcccg acgatgacgc cggtgaactt cccgccgccg ttgttgtttt    2100
ggagcacgga aagacgatga cggaaaaaga gatcgtggat tacgtcgcca gtcaagtaac    2160
aaccgcgaaa aagttgcgcg gaggagttgt gtttgtggac gaagtaccga aaggtcttac    2220
cggaaaactc gacgcaagaa aaatcagaga gatcctcata aaggccaaga agggcggaaa    2280
gtccaaattg aaaccggtcg ccaccatggt gagcaagggc gaggagctgt tcaccggggt    2340
ggtgcccatc ctggtcgagc tggacggcga cgtaaacggc cacaagttca gcgtgtccgg    2400
cgagggcgag ggcgatgcca cctacggcaa gctgaccctg aagttcatct gcaccaccgg    2460
caagctgccc gtgccctggc ccaccctcgt gaccaccctg acctacggcg tgcagtgctt    2520
cagccgctac cccgaccaca tgaagcagca cgacttcttc aagtccgcca tgcccgaagg    2580
ctacgtccag gagcgcacca tcttcttcaa ggacgacggc aactacaaga cccgcgccga    2640
ggtgaagttc gagggcgaca ccctggtgaa ccgcatcgag ctgaagggca tcgacttcaa    2700
ggaggacggc aacatcctgg ggcacaagct ggagtacaac tacaacagcc acaacgtcta    2760
tatcatggcc gacaagcaga agaacggcat caaggtgaac ttcaagatcc gccacaacat    2820
cgaggacggc agcgtgcagc tcgccgacca ctaccagcag aacacccccca tcggcgacgg    2880
ccccgtgctg ctgcccgaca accactacct gagcacccag tccgccctga gcaaagaccc    2940
caacgagaag cgcgatcaca tggtcctgct ggagttcgtg accgccgccg ggatcactct    3000
cggcatggac gagctgtaca agtccggccg gactcagatc tcgagctcaa gcttcgaatt    3060
catgcccacg ctactgcggg tttatataga cggtccccac gggatgggga aaaccaccac    3120
cacgcaactg ctggtggccc tgggttcgcg cgacgatatc gtctacgtac ccgagccgat    3180
gacttactgg cgggtgctgg gggcttccga gacaatcgcg aacatctaca ccacacaaca    3240
ccgcctcgac cagggtgaga tcggccgg ggacgcggcg gtggtaatga caagcgccca    3300
gataacaatg gcatgccctt atgccgtgac cgacgccgtt ctggctcctc atatcggggg    3360
ggaggctggg agctcacatg ccccgccccc ggccctcacc ctcatcttcg accgccatcc    3420
catcgccgcc ctcctgtgct acccggccgc gcggtacctt atgggcagca tgaccccccca    3480
ggccgtgctg gcgttcgtgg ccctcatccc gccgaccttg cccggcacca acatcgtgct    3540
tggggccctt ccggaggaca gacacatcga ccgcctggcc aaacgccagc gcccccggcga   3600
gcggctggac ctggctatgc tggctgcgat tcgccgcgtt tacgggctac ttgccaatac    3660
ggtgcggtat ctgcagtgcg gcgggtcgtg gcgggaggac tggggacagc tttcggggac    3720
ggccgtgccg ccccagggtg ccgagcccca gagcaacgcg ggcccacgac ccatatcgg    3780
ggacacgtta tttaccctgt ttcggcccc cgagttgctg gccccaacg gcgacctgta    3840
taacgtgttt gcctgggcct tggacgtctt ggccaaacgc ctccgttcca tgcacgtctt    3900
tatcctggat tacgaccaat cgcccgccgg ctgccgggac gccctgctgc aacttacctc    3960
cgggatggtc cagacccacg tcaccacccc cggctccata ccgacgatat gcgacctggc    4020
gcgcacgttt gcccgggaga tgggggaggc taacggatcc accggatcta gataa         4075
```

<210> SEQ ID NO 2
<211> LENGTH: 28
<212> TYPE: DNA
<213> ORGANISM: Artificial Sequence
<220> FEATURE:
<223> OTHER INFORMATION: A primer to amplify the transgene.

```
<220> FEATURE:
<221> NAME/KEY: Primer
<222> LOCATION: (1)..(28)

<400> SEQUENCE: 2
ttgaccggtc accatggaag acgccaaa                                        28

<210> SEQ ID NO 3
<211> LENGTH: 22
<212> TYPE: DNA
<213> ORGANISM: Artificial Sequence
<220> FEATURE:
<223> OTHER INFORMATION: A primer to amplify the transgene.
<220> FEATURE:
<221> NAME/KEY: Primer
<222> LOCATION: (1)..(22)

<400> SEQUENCE: 3
cgtcgccgtc cagctcgacc ag                                              22
```